United States Patent [19]
Allen et al.

[11] Patent Number: 5,886,178
[45] Date of Patent: Mar. 23, 1999

[54] 3-AROYLBENZYLPYRIDAZINONE DERIVATIVES

[75] Inventors: Darin A. Allen, Mountain View; James P. Dunn, Los Altos; Eric B. Sjogren, Mountain View; David B. Smith, San Mateo, all of Calif.

[73] Assignee: Syntex (U.S.A.) Inc., Palo Alto, Calif.

[21] Appl. No.: 864,708

[22] Filed: May 28, 1997

Related U.S. Application Data

[60] Provisional application No. 60/018,672 May 30, 1996.
[51] Int. Cl.$^6$ .................. C07D 237/04; A61K 31/50
[52] U.S. Cl. .................. 544/238; 544/114; 514/252
[58] Field of Search .................. 544/238, 114; 514/252

[56] References Cited

U.S. PATENT DOCUMENTS

| 3,752,826 | 8/1973 | Carson | 260/326.3 |
| 5,622,948 | 4/1997 | Dunn et al. | 514/235.5 |

FOREIGN PATENT DOCUMENTS 0 488 602 A1   6/1992   European Pat. Off. .

OTHER PUBLICATIONS

Leuders et al., (CA 112:235333, DE 3818848).
Kim et al., (J. Pharm. Sci., vol. 83 (3), pp. 433–488, 1994).

*Primary Examiner*—Jose' G. Dees
*Assistant Examiner*—Sabiha Qazi
*Attorney, Agent, or Firm*—Rekha Bansal; Rohan Peries

[57] ABSTRACT

Compounds of formula I:

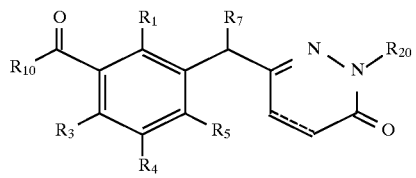

where:

$R_{10}$ is a group represented by formula (A), (B), or (C):

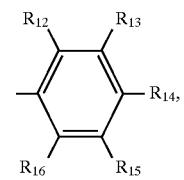

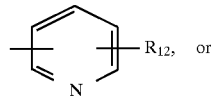

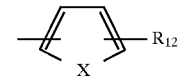

and the other substituents are as defined in the specification;

and their pharmaceutically acceptable salts are inhibitors of prostaglandin G/H synthase and are anti-inflammatory and analgesic agents.

26 Claims, No Drawings

3-AROYLBENZYLPYRIDAZINONE DERIVATIVES

BACKGROUND OF THE INVENTION

Cross-reference to Related Application

This application claims the benefit under 35 U.S.C. 119(e) of U.S. Provisional Application No. 60/018,672, filed May 30, 1996.

1. Field of the invention

This invention relates to anti-inflammatory and analgesic compounds; especially to certain 3-aroylbenzylpyridazinones derivatives, pharmaceutical compositions containing them, methods for their use and methods for preparing these compounds.

2. Description of the Related Art

U.S. Pat. No. 3,752,826 (Carson) discloses 5-aroylpyrrol-2-ylalkanoic acids and derivatives useful as anti-inflammatory agents.

European Patent Application Publication No. 0 071 399 (Syntex (U.S.A.) Inc.) discloses 2-benzyl-5-phenylpyrrolidine derivatives and analogs useful as cardiovascular agents and bronchodilators.

SUMMARY OF THE INVENTION

In a first aspect, this invention provides compounds selected from the compounds represented by formula I:

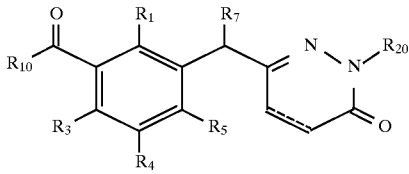

where:
the dashed line denotes an optional bond;
$R_1$ is H, halo, alkyl, alkyloxy, amino, alkylamino, dialkylamino, or acylamino;
$R_3$ and $R_4$ are independently H, halo, alkyl, alkyloxy, or hydroxy;
$R_5$ is H, halo, allyl, alkylthio, alkyloxy, alkenyloxy, alkynyl, or alkenyl; provided that at least one of $R_1$, $R_3$, $R_4$, and $R_5$ is H;
$R_7$ is H, alkyl, cyano, or amido;
$R_{10}$ is a group represented by formula (A), (B), or (C):

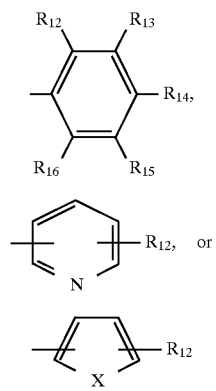

where:
X is O or S;

$R_{12}$, $R_{13}$, $R_{15}$, and $R_{16}$ are independently H, halo, alkyl, alkyloxy, or alkylthio; and $R_{14}$ is H, halo, alkyl, alkylthio, alkyloxy, alkenyloxy, alkynyl, alkenyl, —$SO_2R_{17}$ where $R_{17}$ is alkyl, or —$SO_2NR_{18}R_{19}$ where $R_{18}$ and $R_{19}$ are independently H or alkyl; provided that at least two of $R_{12}$, $R_{13}$, $R_{14}$, $R_{15}$, and $R_{16}$ are H, and that if only two of $R_{12}$, $R_{13}$, $R_{14}$, $R_{15}$, and $R_{16}$ are H, the non-hydrogen substituents are not all adjacent; and at least one of $R_{12}$ and $R_{16}$ is H when neither $R_1$ nor $R_3$ are H; and $R_{20}$ is H, alkyl, haloalkyl, hydroxyalkyl, or alkenyl; and their pharmaceutically acceptable salts.

In a second aspect, this invention provides pharmaceutical compositions containing a therapeutically effective amount of a compound of formula I or its pharmaceutically acceptable salt and a pharmaceutically acceptable excipient.

In a third aspect, this invention provides a method of treatment of a disease, in particular an inflammatory or autoimmune disease, in a mammal treatable by administration of a prostaglandin G/H synthase inhibitor, comprising administration of a therapeutically effective amount of a compound of formula I or its pharmaceutically acceptable salt.

DETAILED DESCRIPTION OF THE INVENTION

Definitions

Unless otherwise stated, the following terms used in the specification and claims have the meanings given below:

"Alkyl" means a linear saturated monovalent hydrocarbon radical of one to six carbon atoms, or a branched or cyclic saturated monovalent hydrocarbon radical of three to six carbon atoms, e.g., methyl, ethyl, propyl, 2-propyl, cyclopropyl, cyclopropylmethyl, pentyl, and the like.

"Alkyloxy" means a radical —OR where R is alkyl, e.g., methoxy, ethoxy, propoxy, 2-propoxy, and the like.

"Alkylthio" means a radical —SR where R is alkyl, e.g., methylthio, butylthio, and the like.

"Alkenyl" means a linear monovalent hydrocarbon radical of two to six carbon atoms or a branched monovalent hydrocarbon radical of three to six carbon atoms containing a double bond, e.g., ethenyl, propenyl, and the like.

"Alkynyl" means a linear monovalent hydrocarbon radical of two to six carbon atoms or a branched monovalent hydrocarbon radical of three to six carbon atoms containing a triple bond, e.g., ethynyl, propynyl, butynyl, and the like.

"Halo" means fluoro, bromo, chloro and iodo, preferably fluoro and chloro.

"Haloalkyl" means alkyl substituted with one to three fluorine or chlorine atoms, e.g., —$CH_2Cl$, —$CF_3$, —$CH_2CF_3$, —$CH_2CCl_3$, and the like.

"Alkylamino" means a radical —NHR where R is alkyl, e.g., methylamino, (1-methylethyl)amino, and the like.

"Dialkylamino" means a radical -NRR' where R and R' are independently alkyl, e.g., dimethylamino, methylethylamino, di(1-methylethyl)amino, and the like.

"Acylamino" means a radical —NHC(O)R where R is alkyl, e.g., acetylamino, pentanoylamino, and the like.

"Amido" means a radical —C(O)$NR^aR^b$ where $R^a$ and $R^b$ are independently H or alkyl, e.g., where $R^a$ and $R^b$ both are H, the amido group is represented as —C(O)$NH_2$ "Hydroxyalkyl" means a linear monovalent hydrocarbon radical of one to four carbons or a branched monovalent hydrocarbon radical of three or four carbon atoms substituted with one or two hydroxy groups, provided that if two hydroxy groups are present, they are not both on the same carbon atom. Examples include hydroxymethyl, 2-hydroxyethyl, 2-hydroxypropyl, 3-hydroxypropyl, 2-hydroxybutyl, 3- hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Optional" or "optionally" means that the subsequently described event or circumstance may but need not occur, and that the description includes instances where the event or circumstance occurs and instances in which it does not. For example, "optional bond" means that the bond may or may not be present and that the description includes both single and double bonds.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight etc., of the mammal to be treated.

"Me" denotes methyl.

Nomenclature

The naming and numbering of the compounds of this invention is illustrated below. The benzylpyridazinone nucleus of the compounds of formula I is numbered as follows:

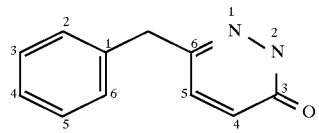

Side chains of the $R_{10}$ substituent are numbered as shown below:

(A)

(B)

(C)

The pyridine, thiophene, and furan rings can be linked to the carbonyl group at any position on the ring other than 1-position. Accordingly, the pyridine ring can be 2-, 3-, or 4-pyridyl, the thiophene ring can be 2- or 3-thienyl, and the furan ring can be 2- or 3-furyl.

The nomenclature used in this application is generally based on the IUPAC recommendations. However, because a strict adherence to these recommendations would result in the names changing substantially when only a single substituent is changed, compounds have been named in a form that maintains consistency of nomenclature for the basic structure of the molecule.

Representative compounds of this invention are as follows

I. Compounds where $R_4=R_{12}=R_{13}=R_{15}=R_{16}=R_{20}=H$ and $R_{10}$ is a group of formula (A) are:

| CPD # | $R_1$ | $R_3$ | $R_5$ | $R_7$ | $R_{14}$ | M. Pt. °C. |
|---|---|---|---|---|---|---|
| 1 | Cl | Cl | H | H | Cl | 228–230.2 |
| 2 | Cl | H | H | H | OMe | 191.8–193 |
| 3 | Cl | H | H | H | Cl | 193.5–194.1 |
| 4 | Cl | H | H | CN | Cl | 228–229.5 |
| 5 | Cl | H | H | H | SMe | 156.9–157.2 |
| 6 | Cl | Cl | H | CN | Cl | 228.7–229.2 |
| 7 | OMe | H | H | H | OMe | 153.8–154.8 |
| 8 | Me | H | Me | H | Cl | 203.5–206 |
| 9 | Me | H | H | H | Cl | 165.1–166.1 |
| 10 | Me | H | H | H | SMe | 150.7–151.9 |
| 11 | Me | H | H | H | OMe | 158.3–158.6 |

-continued

| CPD # | $R_1$ | $R_3$ | $R_5$ | $R_7$ | $R_{14}$ | M. Pt. °C. |
|---|---|---|---|---|---|---|
| 12 | Me | H | H | CN | Cl | 216.9–218 |
| 13 | H | OMe | H | H | Me | 154.8–155.2 |
| 14 | H | OH | H | H | Me | 153.5–155.5 |
| 15 | H | Cl | H | H | OMe | 154–156 |
| 16 | H | Cl | H | CN | OMe | 193.5–196.5 |
| 17 | H | H | H | Me | H | 166.7–167.2 |
| 18 | H | H | H | H | H | 79.7–81 |
| 19 | H | H | H | CN | H | 167.5–168.2 |
| 20 | F | F | H | CN | Me | 147.5–150.5 |
| 21 | F | F | H | H | Me | 169–170 |
| 22 | $NH_2$ | H | H | H | Cl | 234–236 |
| 23 | NHCOMe | H | H | H | Cl | 258 | and are named as follows:
1. 6-[3-(4-chlorobenzoyl)-2,4-dichlorobenzyl]-2H-pyridazin-3-one.
2. 6-[3-(4-methoxybenzoyl)-2-chlorobenzyl]-2H-pyridazin-3-one.
4. {2-[3-(4-chlorobenzoyl)-2-chlorophenyl]-2-(6-oxo-1,6-dihydropyridazin-3-yl)}-acetonitrile.
7. 6-[3-(4-methoxybenzoyl)-2-methoxybenzyl]-2H-pyridazin-3-one.
10. 6-[3-(4-methylthiobenzoyl)-2-methylbenzyl]-2H-pyridazin-3-one.
11. 6-[3-(4-methoxybenzoyl)-2-methylbenzyl]-2H-pyridazin-3-one.
13. 6-[3-(4-methybenzoyl)-4-methoxybenzyl]-2H-pyridazin-3-one.
16. {2-[3-(4-methoxybenzoyl)-4-chlorophenyl]-2-(6-oxo-1,6-dihydropyridazin-3-yl)}-acetonitrile.
21. 6-[3-(4-methylbenzoyl)-2,4-difluorobenzyl]-2H-pyridazin-3-one.
23. 6-[3-(4-chlorobenzoyl)-2-acetamidobenzyl]-2H-pyridazin-3-one.

II. Compounds where $R_1=R_3=R_4=R_{13}=R_{15}=H$, $R_5=OMe$ and $R_{10}$ is a group of formula (A) are:

| CPD # | $R_{12}$ | $R_{14}$ | $R_{16}$ | $R_7$ | $R_{20}$ | M. Pt. °C. |
|---|---|---|---|---|---|---|
| 24 | Cl | F | H | H | H | 175–177 |
| 25 | H | F | Cl | CN | H | 192.1–192.8 |
| 26 | Cl | Cl | Cl | H | H | 178.8–179.9 |
| 27 | Cl | H | Cl | H | H | 156.5–157.6 |
| 28 | Cl | Me | Cl | H | H | 200.7–201.6 |
| 29 | Cl | Me | Cl | H | Me | |
| 30 | Cl | Cl | Cl | CN | H | 238.2–239.3 |
| 31 | Cl | Cl | Cl | H | Me | 149.8–150.5 |
| 32 | Cl | Cl | Cl | $CONH_2$ | H | 276.5–279 |
| 33 | Cl | OMe | Cl | H | H | 125–127 |
| 34 | Cl | Cl | Cl | Me | H | 163.5–164.5 |
| 35 | Cl | $OC_2H_5$ | Cl | H | H | 212–213 |
| 36 | Cl | $OC_3H_7$ | Cl | H | H | 209–210 |
| 37 | F | H | F | H | H | 168.5–169 |
| 38 | Br | H | H | H | H | 158.5–159 |
| 39 | Br | Me | Br | H | H | 214.1–214.3 Hex: EtOAc |
| 40 | H | H | H | Me | H | 140–145 |
| 41 | H | H | H | H | H | 124–124.6 |
| 42 | H | H | H | CN | H | 191.1–192.1 |
| 43 | H | Me | H | H | H | 156–156.7 |
| 44 | Me | Me | Me | H | H | 179–179.4 |
| 45 | Me | H | Me | H | H | 151–153 |
| 46 | Me | OMe | Me | H | H | 185.5–188.8 |
| 47 | Me | $OC_2H_5$ | Me | H | H | 119–124 |
| 48 | OMe | H | OMe | H | H | 158.5–162 | and are named as follows:
24. 6-[3-(2-chloro-4-fluorobenzoyl)-6-methoxybenzyl]-2H-pyridazin-3-one.
26. 6-[3-(2,4,6-trichlorobenzoyl)-6-methoxybenzyl]-2H-pyridazin-3-one.
28. 6-[3-(2,6-dichloro-4-methylbenzoyl)-6-methoxybenzyl]-2H-pyridazin-3-one, m/e=416(M+).
30. {2-[3-(2,4,6-trichlorobenzoyl)-6-methoxyphenyl]-2-(6-oxo-1,6-dihydropyridazin-3-yl)}acetonitrile.
31. 6-[3-(2,4,6-trichlorobenzoyl)-6-methoxybenzyl]-2-methyl-2H-pyridazin-3-one.
35. 6-[3-(2,6-dichloro-4-ethoxybenzoyl)-6-methoxybenzyl]-2H-pyridazin-3-one.
39. 6-[3-(2,6-dibromo-4-methylbenzoyl)-6-methoxybenzyl]-2H-pyridazin-3-one.
41. 6-[3-benzoyl-6-methoxybenzyl]-2H-pyridazin-3-one.
44. 6-[3-(2,4,6-trimethylbenzoyl)-6-methoxybenzyl]-2H-pyridazin-3-one.

III. Compounds where $R_1=R_3=R_4=R_3=R_{15}=H$ and $R_{10}$ is a group of formula (A) are:

| CPD # | $R_5$ | $R_{12}$ | $R_{14}$ | $R_{16}$ | $R_7$ | $R_{20}$ | M. Pt. °C. |
|---|---|---|---|---|---|---|---|
| 49 | allyloxy | Cl | Cl | Cl | H | H | 92–104 |
| 50 | ethoxy | Cl | Cl | Cl | H | H | 163.5–164.3 |
| 51 | cyclopropylmethyloxy | Cl | Cl | Cl | H | H | 173.5–175 |
| 52 | cyclopropylmethyloxy | Cl | Cl | Cl | H | cyclopropylmethyl | 125.3–128.5 |
| 53 | propoxy | Cl | Cl | Cl | H | H | 161.6–162.5 |
| 54 | 2-propoxy | Cl | Cl | Cl | H | H | 102–168 |
| 55 | allyloxy | Cl | Cl | Cl | H | allyl | 127.9–128.7 |
| 56 | propoxy | Cl | Cl | Cl | H | propyl | 135–136 |
| 57 | butoxy | Cl | Cl | Cl | H | butyl | 153.4–157 |
| 58 | ethoxy | Cl | Cl | Cl | H | ethyl | 133.8–134.5 |
| 59 | butoxy | Cl | Cl | Cl | H | H | 103.7–103.9 |
| 60 | 2-methylpropoxy | Cl | Cl | Cl | H | H | 166.5–167 |
| 61 | Me | Cl | Cl | Cl | H | H | 193–193.1 |
| 62 | Me | Cl | Cl | Cl | H | Me | 152–154 |
| 63 | Me | Cl | Cl | Cl | H | ethyl | 133.2–135 |
| 64 | Me | Cl | Cl | Cl | H | butyl | 115–117 |
| 65 | Me | Cl | Cl | Cl | H | propyl | 104.5–106 |
| 66 | Me | Cl | Cl | Cl | H | allyl | 108–109 |
| 67 | Me | Cl | Cl | Cl | Me | Me | 153.7–156.6 |
| 68 | Me | Cl | Cl | Cl | H | 2-fluoroethyl | 153.5–154.5 |
| 69 | Me | Cl | SMe | Cl | H | H | 215–216.3 |
| 70 | Me | SMe | SMe | Cl | H | H | 257–259.5 |
| 71 | SMe | Cl | Cl | Cl | H | H | 216.6–218.3 |
| 72 | SMe | Cl | SMe | Cl | H | H | 204.5–208 |
| 73 | Cl | cl | Cl | Cl | H | H | 182.2–184.8 |
| 74 | Cl | Cl | Cl | Cl | Me | H | 185.2–186.9 |
| 75 | Cl | Cl | Cl | Cl | H | Me | 115–117 |
| 76 | Cl | Cl | Cl | Cl | Me | Me | 133.3–135 |
| 77 | F | Cl | Cl | Cl | H | H | 185–185.3 |
| 78 | H | Cl | Cl | Cl | H | H | 149–151 |
| 79 | H | Cl | H | Cl | H | H | 146–150 |
| 80 | OH | Cl | Cl | Cl | H | H | 257.8 |
| 81 | Me | Cl | Cl | Cl | Me | H | 221.2–222.3 |
| 82 | OMe | Cl | H | Cl | H | H | 188–188.4 | and are named as follows:
49. 6-[3-(2,4,6-trichlorobenzoyl)-6-allyloxybenzyl]-2H-pyridazin-3-one.
53. 6-[3-(2,4,6-trichlorobenzoyl)-6-propoxybenzyl]-2H-pyridazin-3-one.
57. 6-[3-(2,4,6-trichlorobenzoyl)-6-butoxybenzyl]-2-butyl-2H-pyridazin-3-one.
61. 6-[3-(2,4,6-trichlorobenzoyl)-6-methylbenzyl]-2H-pyridazin-3-one.
62. 6-[3-(2,4,6-trichlorobenzoyl)-6-methylbenzyl]-2-methyl-2H-pyridazin-3-one.
63. 6-[3-(2,4,6-trichlorobenzoyl)-6-methylbenzyl]-2-ethyl-2H-pyridazin-3-one.
67. 6-{1-[3-(2,4,6-trichlorobenzoyl)-6-methylphenyl]ethyl}-2-methyl-2H-pyridazin-3-one.
68. 6-[3-(2,4,6-trichlorobenzoyl)-6-methylbenzyl]-2-(2-fluoroethyl)-2H-pyridazin-3-one.

70. 6-[3-(2,4-bis(methylthio)-6-chlorobenzoyl)-6-methylbenzyl]-2H-pyridazin-3-one.
73. 6-[3-(2,4,6-trichlorobenzoyl)-6-chlorobenzyl]-2H-pyridazin-3-one.
74. 6-{1-[3-(2,4,6-trichlorobenzoyl)-6-chlorophenyl]ethyl}-2H-pyridazin-3-one.
77. 6-[3-(2,4,6-trichlorobenzoyl)-6-fluorobenzyl]-2H-pyridazin-3-one.
78. 6-[3-(2,4,6-trichlorobenzoyl)benzyl]-2H-pyridazin-3-one.

PREFERRED COMPOUNDS

While the broadest definition of this invention is set forth in the Summary of the Invention, certain compounds of formula I are preferred. For example, preferred compounds of formula I include those where $R_4$, $R_{12}$, $R_{13}$, $R_{15}$, and $R_{16}$ are H; and further where:

(1) $R_1$ is H, halo, or alkyl; preferably H, Cl, or Me; more preferably Cl or Me;
(2) $R_3$ is H, halo, or alkyl; preferably H, Cl, or Me; more preferably H;
(3) $R_5$ is H, halo, alkyl, alkylthio, or alkyloxy; preferably H, Cl, Me, SMe, or OMe; more preferably H;
(4) $R_7$ is H or cyano, preferably H;
(5) $R_{10}$ is a group represented by the formula (A);
(6) $R_{14}$ is H, halo, alkyl, alkylthio, or alkyloxy; preferably H, Cl, Me, SMe, or OMe; more preferably SMe, OMe, or Cl; most preferably OMe;
(7) $R_{20}$ is H or alkyl; preferably H or Me; more preferably H; and
(8) the optional bond is present;

Other preferred compounds include those where $R_1$, $R_3$, $R_4$, $R_{13}$ and $R_{15}$ are H; and further where:

(1) $R_5$ is H, halo, alkyl, alkylthio, or alkyloxy; preferably H, F, Cl, Me, SMe, or OMe; more preferably H, F, Cl, Me, or OMe; most preferably F or OMe;
(2) $R_7$ is H, or alkyl; preferably H or Me; more preferably H;
(3) $R_{10}$ is a group represented by the formula (A);
(4) $R_{12}$ and $R_{16}$ are H, halo, or alkyl; preferably H, Cl, Br, or Me; more preferably Cl or Me;
(5) $R_{14}$ is H, halo, alkyl, alkylthio, or alkyloxy; preferably H, Cl, Me, SMe, or OMe; more preferably Cl, Me, or OMe; most preferably Cl or Me;
(6) $R_{20}$ is H or alkyl; preferably H or Me; more preferably H; and
(7) the optional bond is present.

A number of different substituent preferences have been given in the list above, and following any of these substituent preferences results in a compound of this invention that is more preferred than one in which the particular substituent preference is not followed. However, these substituent preferences are generally independent, although some preferences are mutually exclusive, and following more than one of the substituent preferences results in a more preferred compound than one in which fewer of the substituent preferences are followed. Thus, particularly preferred compounds of this invention are those in which (to the extent possible) most of the above preferences are followed. Exemplary particularly preferred compounds are:

6-[3-(4-methoxybenzoyl)-2-methylbenzyl]-2H-pyridazin-3-one.
6-[3-(2,4,6-trichlorobenzoyl)benzyl]-2H-pyridazin-3-one.
6-[3-(2,4,6-trichlorobenzoyl)-6-fluorobenzyl]-2H-pyridazin-3-one.
6-[3-(2,4,6-trichlorobenzoyl)-6-chlorobenzyl]-2H-pyridazin-3-one.
6-[3-(2,4,6-trichlorobenzoyl)-6-methylbenzyl]-2H-pyridazin-3-one.
6-[3-(2,4,6-trichlorobenzoyl)-6-methylbenzyl]-2-methyl-2H-pyridazin-3-one.
6-[3-(2,6-dichloro-4-methylbenzoyl)-6-methoxybenzyl]-2H-pyridazin-3-one.
6-[3-(2,4,6-trichlorobenzoyl)-6-methoxybenzyl]-2-methyl-2H-pyridazin-3-one.
6-[3-(2,6-dibromo-4-methylbenzoyl)-6-methoxybenzyl]-2H-pyridazin-3-one
6-[3-(2,4,6-trimethylbenzoyl)-6-methoxybenzyl]-2H-pyridazin-3-one.
6-[3-(2,4,6-trichlorobenzoyl)-6-methoxybenzyl]-2H-pyridazin-3-one.
6-[3-(4-methoxybenzoyl)-2-chlorobenzyl]-2H-pyridazin-3-one.

GENERAL SYNTHETIC SCHEME

Compounds of this invention can be made by the methods depicted in the reaction schemes shown below.

The starting materials and reagents used in preparing these compounds are either available from commercial suppliers such as Aldrich Chemical Co., or are prepared by methods known to those skilled in the art following procedures set forth in references such as *Fieser and Fieser's Reagents for Organic Synthesis*, Volumes 1–15 (John Wiley and Sons, 1991); *Rodd's Chemistry of Carbon Compounds*, Volumes 1–5 and Supplementals (Elsevier Science Publishers, 1989); and *Organic Reactions*, Volumes 1–40 (John Wiley and Sons, 1991). The following schemes are merely illustrative of some methods by which the compounds of this invention can be synthesized, and various modifications to these schemes can be made and will be suggested to one skilled in the art having referred this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about –78° C. to about 150° C., more preferably from about 0° C. to about 125° C. and most preferably at about room (or ambient) temperature, e.g., about 20° C.

Schemes A, B, and C describe alternate methods to generate the compounds of formula I.

Scheme A

Scheme A describes the synthesis of a compound of formula I from a 3-aroyltoluene.

Step 1

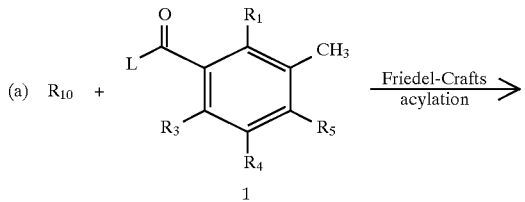

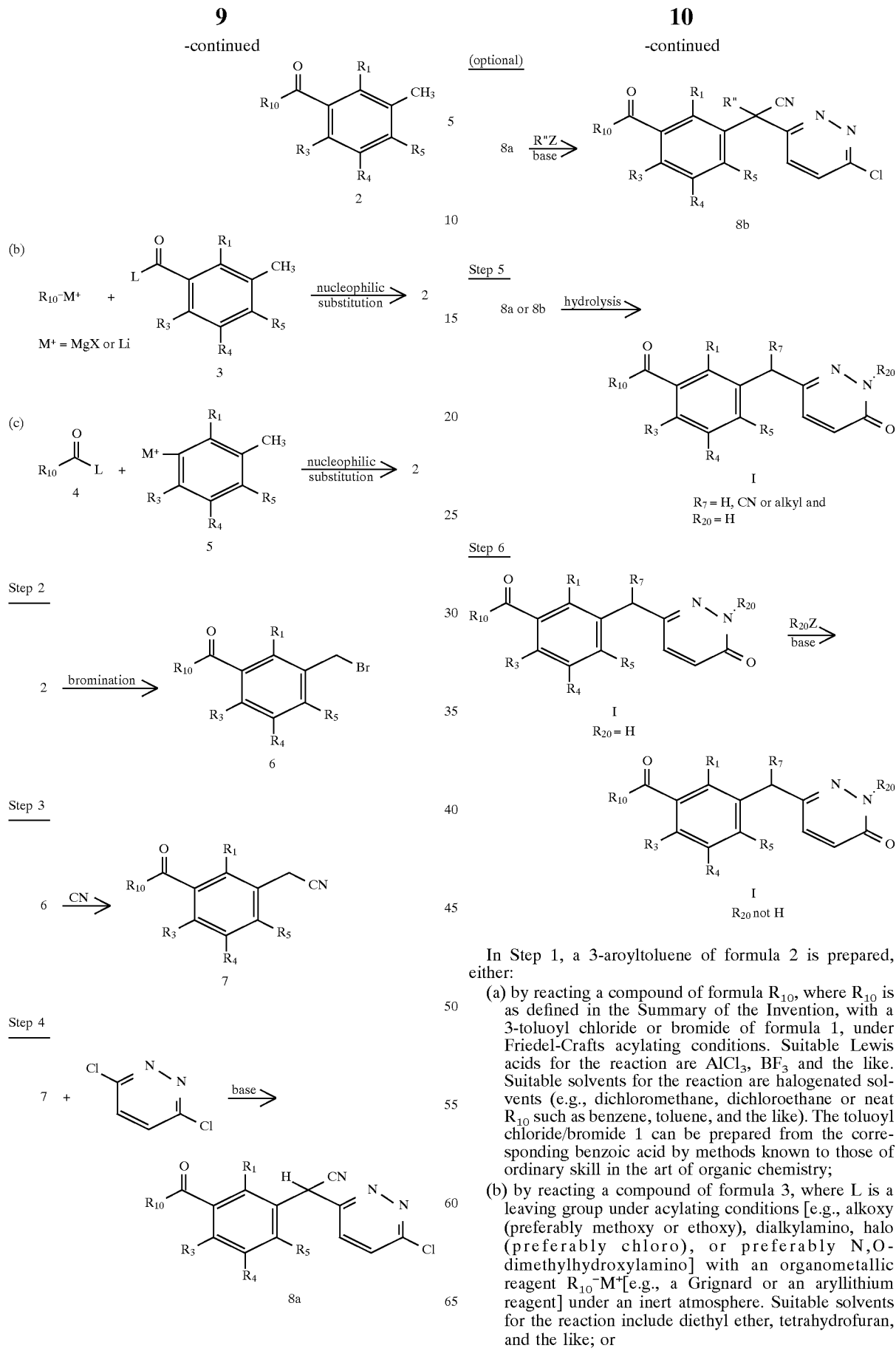

In Step 1, a 3-aroyltoluene of formula 2 is prepared, either:
(a) by reacting a compound of formula $R_{10}$, where $R_{10}$ is as defined in the Summary of the Invention, with a 3-toluoyl chloride or bromide of formula 1, under Friedel-Crafts acylating conditions. Suitable Lewis acids for the reaction are $AlCl_3$, $BF_3$ and the like. Suitable solvents for the reaction are halogenated solvents (e.g., dichloromethane, dichloroethane or neat $R_{10}$ such as benzene, toluene, and the like). The toluoyl chloride/bromide 1 can be prepared from the corresponding benzoic acid by methods known to those of ordinary skill in the art of organic chemistry;
(b) by reacting a compound of formula 3, where L is a leaving group under acylating conditions [e.g., alkoxy (preferably methoxy or ethoxy), dialkylamino, halo (preferably chloro), or preferably N,O-dimethylhydroxylamino] with an organometallic reagent $R_{10}{}^-M^+$[e.g., a Grignard or an aryllithium reagent] under an inert atmosphere. Suitable solvents for the reaction include diethyl ether, tetrahydrofuran, and the like; or (c) by proceeding as described in method (b) but substituting an organometallic reagent of formula 5 and an acylating reagent of formula 4 for compounds $R_{10}^{-}M^{+}$ and 3 respectively. Exemplary preparations of a 3-aroyltoluene utilizing the reaction conditions described above are given in Examples 1 (a), (b), and (c).

Depending upon the nature of the substituents on the 3-aroyltoluene 2 and the availability of the starting materials, one of the above described methods may be preferable over the others, e.g., in the synthesis of 3-benzoyl-2,4-dichlorotoluene, the method of Step 1(c) would be preferable because of the ease of generating the anion at the 3-position in 2,4-dichlorotoluene which can then be reacted with the N,O-dimethylbenzamide to give the desired product.

3-Methylbenzoic acid and its analogs are commercially available or may be prepared using minor modifications of the method described in Iwao, M.; J. Org. Chem., 1990, 55, 3622–3627. The preparation of 2-chloro-3-methylbenzoic acid by this method is described in Example 1(a).

In step 2, a 3-aroylbenzyl bromide 6 is prepared by benzylic bromination of the 3-aroyltoluene 2 by a suitable brominating agent such as N-bromosuccinimide. The bromination proceeds upon heating in the presence of a free radical initiator such as benzoyl peroxide under an inert atmosphere (e.g., argon or nitrogen, preferably nitrogen). Suitable solvents for the reaction are chlorinated or aromatic hydrocarbons such as $CCl_4$ and benzene.

In step 3, a (3-aroylphenyl)acetonitrile 7 is prepared by nucleophilic substitution of the bromo group in the 3-aroylbenzyl bromide 6 by a cyanide ion. The substitution is effected by reacting compound 6 with a cyanide salt (e.g., KCN or NaCN) in a suitable polar aprotic solvent such as dimethyl sulfoxide, aqueous dioxane, or dimethylformamide.

In step 4, a 2-{(3-aroylphenyl)-2-(6-chloropyridazin-3-yl)}acetonitrile 8a, is prepared by nucleophilic substitution of the chloro group in 3,6-dichloropyridazine by the compound of formula 7. The reaction is carried in the presence of a strong base (e.g., sodium or potassium hydride, lithium diisopropylamide and the like) under an inert atmosphere. Suitable solvents for the reaction are aprotic organic solvents such as dimethylformamide, N-methyl pyrrolidone, THF, and the like. Additionally, if a compound of formula I having $R_7$ as an alkyl group is desired, then the alkyl group can be introduced in Step 4 by reacting compound 8a with an alkylating agent R"Z, where Z is a leaving group under alkylating conditions (e.g., bromo, iodo, mesylate, triflate, and the like) in the presence of a base such as sodium hydride and in an aprotic organic solvent.

In step 5, a 6-(3-aroylbenzyl)-2H-pyridazin-3-one of formula I can be prepared from 8a or 8b under hydrolysis conditions. If a compound of formula I having a cyano group as $R_7$ is desired, the hydrolysis of compound 8a is carried out in the presence of a weak base such as sodium acetate in glacial acetic acid thus leaving the cyano group intact. If a compound of formula I having a hydrogen or an alkyl group as $R_7$ is desired, the hydrolysis/decarboxylation of the cyano group is carried out by heating compound 8a or 8b in the presence of either a strong aqueous acid such as HCl in glacial acetic acid or an aqueous base (e.g., LiOH, KOH, and the like) in a suitable organic solvent such as dioxane. If the decarboxylation does not occur under the basic reaction conditions, it may be effected by acidifying the reaction mixture to give the free acid, which decarboxylates either at ambient temperature or upon heating.

In Step 6, a compound of formula I, where $R_{20}$ is not hydrogen can be prepared by reacting a corresponding compound of formula I where $R_{20}$ is H with an alkylating agent $R_{20}Z$ where Z is a leaving group under alkylating conditions (e.g., bromo, iodo, mestylate, triflate, and the like). The reaction is carried out in the presence of a base (e.g., potassium carbonate, cesium carbonate, and the like) in an aprotic organic solvent (e.g., THF, acetone, DMF, and the like).

The preparation of a 6-{(3-aroylbenzyl)-2H-pyridazin-3-one (where $R_7$ is H) by this method is described in detail in Example 2 and the conversion of a compound of formula I where $R_7$ is H to a corresponding compound of formula I where $R_{20}$ is methyl is described in Example 5.

Scheme B

Scheme B describes the synthesis of a compound of formula I from a 2-phenylacetate where $R_5$ is an ortho-para directing group in a Friedel-Crafts reaction.

Step 1

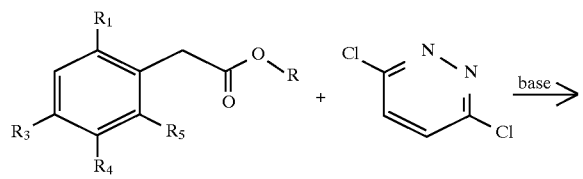

10

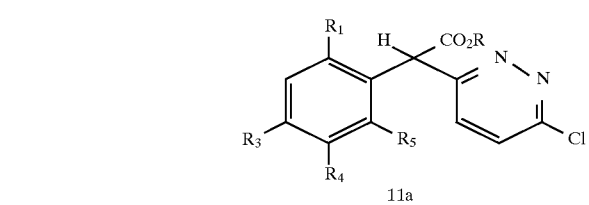

11a (optional)

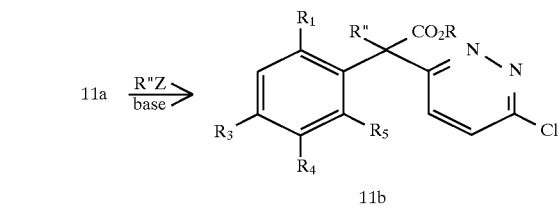

11a $\xrightarrow{R"Z}{base}$

11b

Step 2

11a or 11b $\xrightarrow{aq.\ base}{heat}$

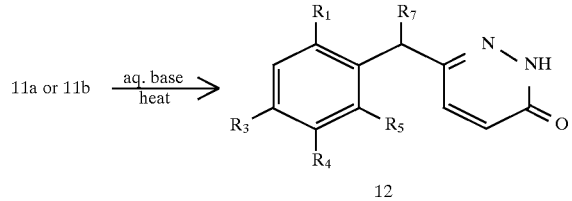

12
$R_7$ = H or alkyl

Step 2 (alternative)

11a or 11b $\xrightarrow{aq.\ base}{room\ temp}$

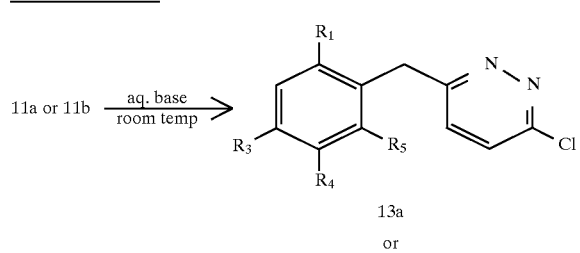

13a
or

-continued

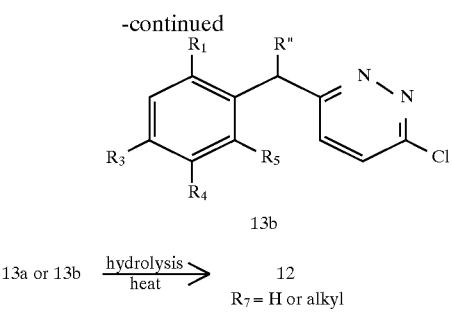

13a or 13b $\xrightarrow[\text{heat}]{\text{hydrolysis}}$ 12

$R_7$ = H or alkyl

Step 3

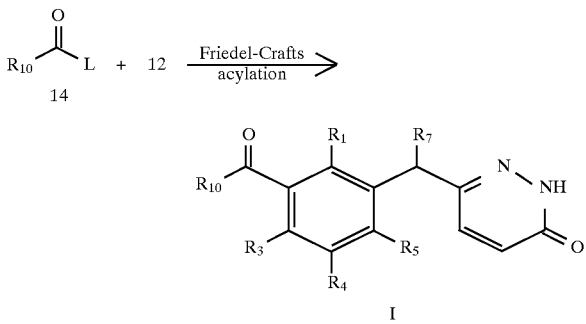

Step 4

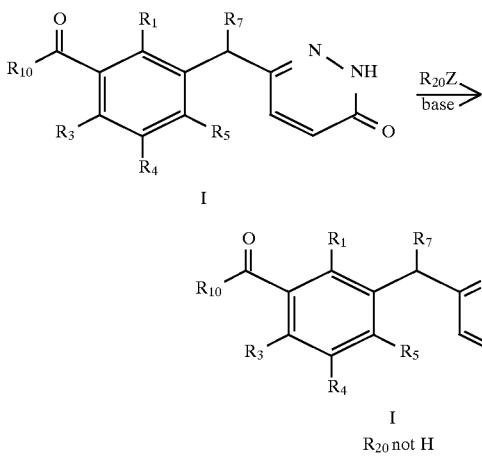

In Step 1, a 2-phenyl-2-(6-chloropyridazin-3-yl)acetate 11a or 11b is prepared by proceeding as described in Step 4 of Scheme A, but substituting a 2-phenylacetate of formula 10 for a compound of formula 7.

In Step 2, a 6-benzylpyridazin-3-one 12, where $R_7$ is H or alkyl is prepared by hydrolysis and decarboxylation of the ester group in compound 11a and 11b respectively. The hydrolysis/decarboxylation proceeds upon heating, in the presence of an aqueous base (e.g., LiOH, NaOH and the like) and in a suitable organic solvent such as dioxane. If the decarboxylation does not occur under the basic conditions, it is effected by acidifying the reaction mixture to give the free acid which decarboxylates either at ambient temperature or upon heating. The above hydrolysis/decarboxylation reaction conditions also causes the hydrolysis of the 3-chloropyridazine ring to pyridazin-3-one.

Alternatively, Step 2 can be carried out in two steps as shown in Step 2 (alternative), by first carrying out the hydrolysis and decarboxylation of the ester group in the presence of an aqueous base at ambient temperature to obtain a 6-benzyl-3-chloropyridazine of the formula 13a or 13b, which is then converted to the 6-benzylpyridazin-3-one 12 by proceeding as described in Step 5 of Scheme A. In this two-step process, a compound of formula 13b can also be prepared from a corresponding compound of formula 13a, by reacting 13a with an alkylating agent R"Z, utilizing the reaction conditions described in Step 4 of Scheme A. The conversion of a compound of formula 13a where $R_7$ is H to a corresponding compound of formula 13b where $R_7$ is methyl is described in detail in Example 4.

In Step 3, a compound of formula I is prepared by proceeding as described in Step 1(a) of Scheme A but substituting a compound of formula 12 and an acyl halide 14 where L is chloro or bromo group for compounds $R_{10}$ and 1 respectively.

In Step 4, a compound of formula I where $R_{20}$ is not hydrogen can be prepared by proceeding as described in Step 6 of Scheme A. The preparation of a 6-(3-aroylbenzyl)-pyridazin-3-one (where $R_7$ is H) by this method is described in detail in Example 3.

Scheme B is particularly suited for preparing compounds of formula I having $R_5$ as an ortho-para directing group under Friedel-Crafts reaction conditions and compounds of formula I having any of $R_4$, $R_{12}$, $R_{13}$, $R_{14}$, $R_{15}$, and $R_{16}$ as the methyl group.

Alternatively, a compound of formula I can also be prepared from a 2-phenylacetate, where $R_5$ is an ortho/para directing group in a Friedel-Crafts reaction as shown in Scheme C.

Scheme C

Step 1

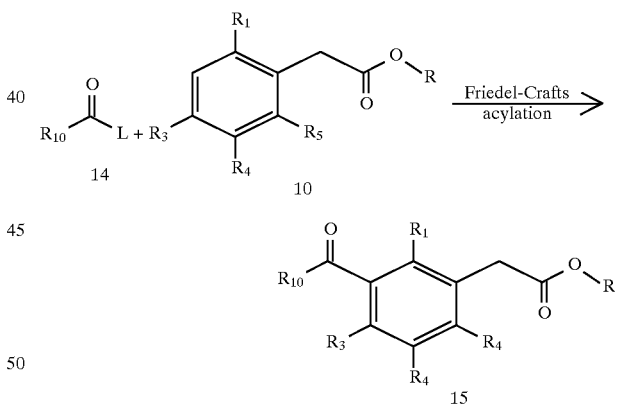

Step 2

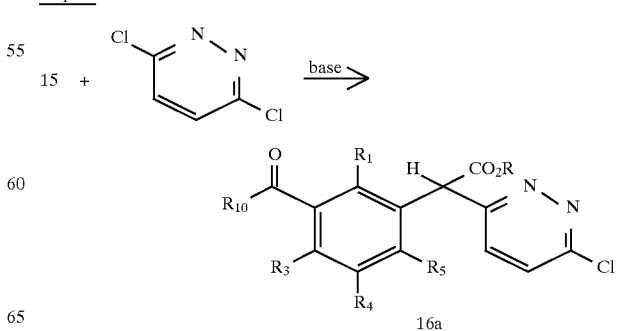

-continued
Scheme C (optional)

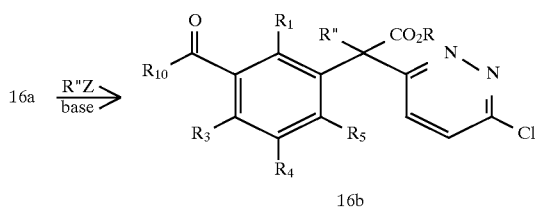

Step 3

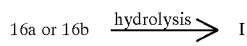

In Step 1, a 3-aroylphenylacetate 15 is prepared by carrying out the acylation step as described in Step 1(a) of Scheme A but substituting a 2-phenylacetate of formula 10 and an acyl halide 14 for compounds of formula 1 and $R_{10}$ respectively.

In Step 2, a 2-(3-aroylphenyl)-2-(6-chloropyradizin-3-yl) acetate 16a or 16b is prepared by proceeding as described in Step 4 of Scheme A but substituting the compound of formula 15 for a compound of formula 7.

A compound of formula I, where $R_{20}$ is H is then prepared from compound 16a or 16b by carrying out the hydrolysis/decarboxylation of the ester group and the hydrolysis of the chloropyridazine ring to the pyridazinone, utilizing the reaction conditions described in Step 2 or Step 2 (alt.) of Scheme B. A compound of formula I where $R_{20}$ is not hydrogen may be prepared by methods described in Step 6 of Scheme A.

Additional Processes

Compounds of formula I having a group that would be unstable under the reaction conditions utilized in Schemes A-C can be prepared by modification of another group present on a corresponding compound of formula I, e.g.; a compound of formula I containing an alkenyloxy or other alkyloxy groups may be prepared by de-alkylation/alkylation of the methoxy substituent on the corresponding compound of formula I. The conversion of a compound of formula I where $R_5$ is methoxy to a corresponding compound of formula I where $R_5$ is ethoxy by the dealkylation/alkylation procedure is described in Example 6. A compound of formula I can also be prepared by substitution of a group present on a corresponding compound of formula I e.g.; a compound of formula I where $R_{14}$ is methylthio may be prepared by substitution of a chlorine atom on a corresponding compound of formula I and a compound of formula I where $R_5$ is H may be prepared by dehalogenation of the corresponding halo group in a compound of formula I. The conversion of a compound of formula I where $R_{14}$ is chloro to a corresponding compound of formula I where $R_{14}$ is methylthio is described in Example 7. The conversion of a compound of formula I where $R_5$ is bromo to a corresponding compound of formula I where $R_5$ is hydrogen is described in Example 8.

General Utility

The compounds of the invention are inhibitors of prostaglandin G/H Synthase I and II (COX I and COX II), especially COX II, in vitro, and as such, are expected to possess both anti-inflammatory and analgesic properties in vivo. The compounds, and compositions containing them, are therefore useful as anti-inflammatory and analgesic agents in mammals, especially humans. They find utility in the treatment of inflammation and pain caused by diseases such as arthritis, gout, and autoimmune disorders (such as systemic lupus erythematosus, rheumatoid arthritis, and type I diabetes).

As inhibitors of prostaglandin G/H Synthase, the compounds of this invention are also expected to be useful in the prevention and treatment of cancer, in particular colon cancer. It has been shown that drugs that inhibit prostaglandin G/H Synthase are effective in animal models of cancer and that COX-2 gene expression is upregulated in human colorectal cancers (Eberhart, C. E., et. al.; Gastroenterology, (1994), 107, 1183–1188 and Ara, G., and Teicher, B.A., Prostaglandins, Leukotrienes and Essential Fatty Acids, (1996), 54, 3–16). In addition, there is epidemiological evidence that shows a correlation between use of drugs that inhibit prostaglandin G/H synthase and a reduced risk of developing colorectal cancer, (Heath, C. W. Jr., et. al.; Cancer, (1994), 74, No. 10, 2885–8).

The compounds of this invention are also expected to be useful in the prevention and treatment of Alzheimer's disease. Indomethacin, an inhibitor of prostaglandin G/H synthase, has been shown to inhibit the cognitive decline of Alzheimer's patients, (Rogers, J., et. al., Neurology, (1993), 43, 1609). Also, the use of drugs which inhibit prostaglandin G/H synthase has been linked epidemiologically with a delayed onset of Alzheimer's disease, (Breitner, J. C. S., et. al., Neurobiology of Aging, (1995), 16, No. 4, 523 and Neurology, (1994), 44, 2073).

Testing

The anti-inflammatory activity of the compounds of this invention may be assayed by measuring the ability of the compound to inhibit COX I and COX II, especially COX II in vitro using a radiometric assay, as described in more detail in Example 10 and 11. It may also be assayed by in vivo assays such as the Rat Carrageenan Paw and Rat Air-Pouch assays, as described in more detail in Examples 12 and 13. The analgesic activity of the compounds of this invention may be assayed by in vivo assays such as the Acetic acid induced Rat Writhing Assay and the rat arthritis pain model as described in more detail in Example 14.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of formula I may range from approximately 0.1–75 mg per Kilogram body weight of the recipient per day; preferably about 5–20 mg/Kg/day. Thus, for administration to a 70 Kg person, the dosage range would preferably be about 350 mg to 1.4 g per day.

In general, compounds of this invention will be administered as pharmaceutical compositions by any one of the following routes: oral, systemic (e.g., transdermal, intranasal or by suppository), or parenteral (e.g., intramuscular, intraveneous or subcutaneous) administration. The preferred manner of administration is oral using a convenient daily dosage regiman which can be adjusted according to the degree of affliction. Compositions can take the form of tablets, pills, capsules, semisolids, powders, sustained release formulations, solutions, suspensions, elixirs, aerosols, or any other appropriate compositions and are comprised of, in general, a compound of formula I in combination with at least one pharmaceutically acceptable excipient. Acceptable excipients are non-toxic, aid administration, and do not adversely affect the therapeutic benefit of the compound of formula I. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01–99.99 wt % of a compound of formula I based on the total formulation, with the balance being one or more suitable pharmaceutical excipients. Preferably, the compound is present at a level of about 1–80 wt %. Representative pharmaceutical formulations containing a compound of formula I are described in Example 9.

EXAMPLES

The following preparations and examples are given to enable those skilled in the art to more clearly understand and to practice the present invention. They should not be considered as limiting the scope of the invention, but merely as being illustrative and representative thereof.

EXAMPLE 1

(a)

Synthesis of 3-(4-methoxybenzoyl)-2-chlorotoluene (Following Scheme A)

A solution of 2-chlorotoluene (14.5 ml, 123.8 mmol) in dry THF (500 ml) was cooled to −100° C. in a diethyl ether/liquid nitrogen bath under a nitrogen atmosphere. sec-BuLi (1.3M in cyclohexane, 100 ml, 1.05 eq.) was added at a rate such that the reaction temperature remained below −90° C. during the addition. Stirring was continued at this temperature for 2 h and then dry $CO_2$ was bubbled rapidly through the solution. After the addition was complete, the milky white reaction mixture was allowed to warm to room temperature and the organic solvent was evaporated in vacuo. The resulting slurry was partitioned between ether and water. The aqueous layer was separated and acidified to pH 2 with concentrated HCl, and the product was extracted into ether. The organic extracts were washed with brine and dried over $MgSO_4$, and the solvent was removed in vacuo to give a white solid. Purification on a silica gel column (25/75/1 EtOAc/hexanes/AcOH), followed by recrystallization from toluene gave 2-chloro-3-methylbenzoic acid (3.08 g, 15%) as a solid, mp 140.9°–141.9° C.

To a suspension of 2-chloro-3-methylbenzoic acid (6.75 g, 39.39 mmol) [prepared as described above] in EtOAc were added a few drops of DMF and oxalyl chloride (5.1 ml, 1.5 eq.). After stirring the reaction mixture for 1.5 h, the solvent was removed in vacuo to give 2-chloro-3-methylbenzoyl chloride, which was used in the next step without further purification.

A solution of 2-chloro-3-methylbenzoyl chloride (18.05 mmol), [prepared as described above] in dry $CH_2Cl_2$ (60 ml) was cooled to 0° C. and $AlCl_3$ (2.41 g, 1 eq.) was added. After ten minutes, anisole (1.96 ml, 1 eq.) was added. The resulting orange colored reaction mixture was allowed to warm to room temperature, stirred for 3 h and then poured on ice. The product was extracted into ether, washed with brine, and dried over $MgSO_4$. The solvent was evaporated in vacuo to give 3-(4-methoxybenzoyl)-2-chlorotoluene (4.55 g, 97% yield) as a solid, mp 64.7°–65.8° C.

(b)

Synthesis of 3-(4-chlorobenzoyl)-2-chlorotoluene (Following Scheme A)

p-Chlorophenylmagnesium bromide (2 ml of 1M THF solution, 1.1 eq.) was added dropwise to a solution of N-methoxy-N-methyl-2-chloro-3-methylbenzamide (0.39 g, 1.83 mmol) in dry THF (8 ml) at 0° C. The reaction mixture was stirred overnight at room temperature, and then quenched with 1M $NH_4Cl$. The product was extracted into ether, washed with 1M $NH_4Cl$, brine, and dried over $MgSO_4$. The solvent was removed in vacuo to give 0.48 g of a white solid, which was suspended in EtOAc/hexanes (10:90) and filtered through a silica gel pad to give 3-(4-chlorobenzoyl)-2-chlorotoluene (0.29 g) as white crystals.

(c)

Synthesis of 3-(4-chlorobenzoyl)-2,4-dichlorotoluene (Following Scheme A)

n-BuLi (1.6M, 76 ml) was added dropwise to a solution of 2,4-dichlorotoluene (16.7 ml, 121 mmol) in dry THF (125 ml) at −78° C. under a nitrogen atmosphere. After 1 h a solution of N-methoxy-N-methyl-4-chlorobenzamide (24.26 g, 1 eq.) in dry THF (50 ml) was added slowly to the reaction mixture and the stirring was continued for an additional 1 h. The reaction was then quenched with 1M $NH_4Cl$, and allowed to room temperature. The solvent was removed in vacuo and the resulting mixture was diluted with ether. The organic layer was separated, washed with 1M $NH_4Cl$, water, and brine, and dried over $MgSO_4$. The solvent was removed in vacuo to give an oil, which upon crystallization from hexanes gave 3-(4-chlorobenzoyl)-2,4-dichlorotoluene (19.98 g) as white crystals, mp 132.0°–135.8° C.

EXAMPLE 2

Synthesis of 6-[3-(4-methoxybenzoyl)-2-chlorobenzyl]-2H-pyridazin-3-one (Following Scheme A)

3-(4-Methoxybenzoyl)-2-chlorotoluene (4.55 g, 17.45 mmol) [prepared by the method described in Example 1(a)]was dissolved in benzene (150 ml), and the solution was purged with nitrogen. N-Bromosuccinimide (3.10 g, 1 eq.) and benzoyl peroxide (0.42 g, 0.1 eq.) were added and the reaction mixture was heated at reflux overnight. Since there was an appreciable amount of unreacted starting material still present in the reaction mixture, additional amounts of N-bromosuccinimide (1.55 g, 0.5 eq.) and benzoyl peroxide (0.21 g, 0.05 eq.) were added, and the heating was continued. After 3 h the reaction mixture was cooled to room temperature, and diluted with ether. The organic layer was separated, washed with water and brine, and dried over MgSO$_4$. The solvent was removed in vacuo to give 7.6 g of an orange oil. Purification by flash chromatography (10/90 EtOAc/hexanes) gave 3-(4-methoxybenzoyl)-2-chlorobenzyl bromide as an oil that slowly crystallized to a solid (5.13 g, 87% yield). $^1$H NMR showed it was approximately 90% pure 3-(4-methoxybenzoyl)-2-chlorobenzyl bromide (4.97 g, 1 eq.) [prepared as described above] was added to a solution of KCN (1.05 g, 1.1 eq.) in dry DMSO (40 ml) under a nitrogen atmosphere. After 30 min the reaction mixture was poured into water (1 L) and the product was extracted into ethyl acetate. The organic extract was washed with water and brine, and dried over MgSO$_4$. The solvent was evaporated in vacuo to give 2-[3-(4-methoxybenzoyl)-2-chlorophenyl]acetonitrile (4.08 g, 98% yield) as an oil.

2-[3-(4-methoxybenzoyl)-2-chlorophenyl]acetonitrile (4.08 g, 14.28 mmol, 1 eq.) [prepared as described above] and 3,6-dichloropyridazine (2.13 g, 1 eq.) were dissolved in DMF (30 ml) and the reaction mixture was cooled to 0° C. under a nitrogen atmosphere. 95% NaH (0.72 g, 2.1 eq.) was added portionwise to the solution. The resulting dark red reaction mixture was stirred at 0° C. for 20 min, then warmed to room temperature and quenched with 1M HCl. The product was extracted into ether; and the extracts were washed with dilute HCl, water, and brine, and dried over MgSO$_4$. The solvent was removed in vacuo, giving 5 g of an orange oil. Purification by flash chromatography (35/65 EtOAc/hexanes) provided pure {2-[3-(4-methoxybenzoyl)-2-chlorophenyl]-2-(6-chloropyridazin-3-yl)}-acetonitrile (3.00 g, 52% yield) as an orange foam.

A mixture of {2-[3-(4-methoxybenzoyl)-2-chlorophenyl]-2-(6-chloropyridazin-3-yl)}-acetonitrile (3.0 g, 7.53 mmol) [prepared as described above], glacial acetic acid (5 ml), concentrated HCl (10 ml), and water (5 ml) was heated at reflux overnight. The reaction mixture was cooled to room temperature and diluted with CH$_2$Cl$_2$ The organic layer was separated and washed with water, dilute NaHCO$_3$ and brine, and dried over MgSO$_4$. The solvent was evaporated in vacuo to give 2.66 g of crude 6-[3-(4-methoxybenzoyl)-2-chlorobenzyl]-2H-pyridazin-3-one as a white foam. Recrystallization from acetone/hexanes gave 6-[3-(4-methoxybenzoyl)-2-chlorobenzyl]-2H-pyridazin-3-one (1.04 g, 39% yield), mp 191.8°–193.0° C.

Proceeding as in Examples 1 and 2 above but replacing 2-chloro-3-methylbenzoic acid with 2,3-dimethylbenzoic acid, gave a 1:1 mixture of 2-{[3-(4-methoxybenzoyl)-2-methyl-phenyl]-2-(6-chloropyridazin-3-yl)acetonitrile and 2-{[2-(4-methoxybenzoyl)-6-methyl-phenyl]-2-(6-chloropyridazin-3-yl)acetonitrile. 2-{[3-(4-Methoxybenzoyl)-2-methylphenyl]-2-(6chloropyridazin-3-yl)acetonitrile was isolated by flash chromatography (30/70 EtOAc/hexanes), and then converted to 6-[3-(4-methoxybenzoyl)-2-methylbenzyl]-2H-pyridazin-3-one, mp 158.3°–158.6° C. by proceeding as described further in Example 2.

EXAMPLE 3

Synthesis of 6-[3-(2,4,6-trichorobenzoyl)-6-fluorobenzyl]-2H-pyridazin-3-one (Following Scheme B)

p-Toluenesulfonic acid (20 mg) was added to a solution of 2-fluorophenyl acetic acid (3.8 g, 24.65 mmol) in methanol (29 ml). After heating the reaction mixture for 1 h on the steam bath, the solvent was removed in vacuo. Filtration through a pad of silica gel (ethyl acetate/hexanes 10/90) gave methyl 2-fluorophenylacetate (4.3 g) as an oil.

Methyl 2-fluorophenyl acetate (3.6 g, 21.4 mmol) [prepared as described above] and 3,6-dichloropyridazine (3.35 g, 21.8 mmol) were dissolved in DMF (20 ml). NaH, 60% in mineral oil (1.86 g, 46.5 mmol ) was added in portions over 1 h. After the addition was complete, the mixture was poured into 1M NaHSO4/ice and the product was extracted into ether. The organic extracts were washed with water and brine, dried over MgSO4, and then concentrated in vacuo. The crude product was chromatographed on a silica gel column (14% ethyl acetate in hexanes, then 25% ethyl acetate in hexanes) to give methyl 2-(2-fluorophenyl) -2-(6-chloropyridazin-3-yl) acetate (4.25 g, 69% yield) as an orange oil, which was used in the next step without further purification.

An aqueous solution of lithium hydroxide (2 g /10 ml of water) was added to a solution of methyl 2-(2-fluorophenyl) -2-(6-chloropyridazin-3-yl)acetate (4.25 g, 14.84 mmol) [prepared as described above] in methanol (30 ml). After 1.5 h, acetic acid (10 ml) was added and the stirring was continued overnight. The product was extracted into ether, and the extract was washed with water, aqueous NaHCO$_3$, and brine, and dried over MgSO$_4$. The solvent was removed in vacuo and the crude was chromatographed on a silica gel column (10% ethyl acetate in hexanes) to give 6-(2-fluorobenzyl)-3-chloropyridazine (2.56 g) as an oil.

6-(2-Fluorobenzyl)-3-chloropyridazine (2.5 g, 11.2 mmol) [prepared as described above] was dissolved in acetic acid (15 ml). Sodium acetate (3.37 g, 24.8 mmol) was added and the reaction mixture was heated at 110° C. under a nitrogen atmosphere. After 1.5 h the reaction mixture was diluted with water and the product was extracted into ethyl acetate. The organic extracts were washed with water, aqueous NaHCO$_3$ and brine, and dried over MgSO$_4$. The solvent was removed in vacuo and the crude product was chromatographed on a silica gel column (50% ethyl acetate in hexanes) to give 6-(2-fluorobenzyl)-2H-pyridazin-3-one (1.5 g, 55% yield) as a yellow solid.

AlCl$_3$ (1.75 g, 13.1 mmol) was added to a solution of 6-(2-fluorobenzyl)-2H-pyridazin-3-one (0.9 g, 4.4 mmol) [prepared as described above] in methylene chloride (20 ml) at ambient temperature and under a nitrogen atmosphere. 2,4,6-trichlorobenzoyl chloride [(1.98 g, 8.78 mmol) prepared from the corresponding acid by treatment with oxalyl chloride/ methylene chloride with a trace of DMF] was added to the slurry. After stirring overnight, the reaction was quenched with ice. The product was extracted into ethyl acetate, and dried over MgSO$_4$. The solvent was removed in vacuo and the crude product was chromatographed on a silica gel column (ether) to give impure 6-[3-(2,4,6-trichlorobenzoyl)-6-fluorobenzyl)-2H-pyridazin-3-one (0.43 g). Recrystallization from acetone/hexanes mixture gave pure 6-[3-(2,4,6-trichlorobenzoyl)-6-fluorobenzyl)-2H-pyridazin-3-one (0.34 g, 18% yield) as a solid, mp 185.0°–185.3° C.

Proceeding as in Example 3, but replacing 2-fluorophenylacetic acid with 2-methoxyphenylacetic acid, gave 6-[3-(2,4,6-trichlorobenzoyl)-6-methoxybenzyl)-2H-pyridazin-3-one, mp 178.8°–179.9° C.

EXAMPLE 4

Synthesis of 6-{1-[3-(2,4,6-trichlorobenzoyl)-6-methylphenyl]ethyl}-2H-pyridazin-3-one NaH (0.461 g, 19.2 mmol) was added to a solution of 6-(2-methylbenzyl)-3-chloropyridazine (2.0 g, 9.15 mmol)

[prepared by proceeding as described in Example 3, but replacing 2-fluorophenylacetic acid with 2-methylphenylacetic acid] in DMF (15 ml). After 5 min MeI (0.7 mL, 10.98 mmol) was added and the stirring was continued for an additional 10 min. The reaction mixture was poured into water, and the product was extracted into ether, and dried over $MgSO_4$. The solvent was removed in vacuo and the crude oil was chromatographed on a silica gel column (15% ethyl acetate in hexanes) to give 6-[1-(2-methylphenyl])ethyl]-3-chloropyridazine (1.0 g) as a solid, which was converted to 6-{1-[3-(2,4,6-trichlorobenzoyl)-6-methylphenyl]ethyl}-2H-pyridazin-3-one by proceeding as described further in Example 3. Recrystallization from acetone/hexanes gave pure 6-{1-[3-(2,4,6-trichlorobenzoyl)-6-methylphenyl]ethyl}-2H-pyridazin-3-one (0.27 g) mp 221.2°–222.3° C.

EXAMPLE 5

Synthesis of 6-[3-(2,4,6-trichlorobenzoyl)-6-methoxybenzyl)-2-methyl-2H-pyridazin-3-one $Cs_2CO_3$ (0.77 g, 2 eq.) and MeI (0.17 g, 1 eq.) were added to a solution of 6-[3-(2,4,6-trichlorobenzoyl)-6-methoxybenzyl)-2H-pyridazin-3-one (0.50 g, 1.18 mmol) [prepared by the method described in Example 3] in dry DMF (2 ml) under a nitrogen atmosphere. After 2.5 h the reaction mixture was diluted with EtOAc. The organic layer was separated and washed with 1M $NaHSO_4$, water and brine and then concentrated in vacuo to give 0.5 g of a greenish oil. Flash chromatography (50/50 to 75/25 EtOAc/hexanes) followed by recrystallization from acetone/hexanes gave 6-[3-(2,4,6-trichlorobenzoyl)-6-methoxybenzyl)-2-methyl-2H-pyridazin-3-one (0.31 g, 60% yield), mp 149.8°–150.5° C.

EXAMPLE 6

Synthesis of 6-[3-(2,4,6-trichlorobenzoyl)-6-ethoxybenzyl]-2H-pyridazin-3-one

Lithium iodide (4.0 g, 29.7 mmol) was added to a solution of 6-[3-(2,4,6-trichlorobenzoyl)-6-methoxybenzyl]-2H-pyridazin-3-one (2.5 g, 5.9 mmol) [prepared by proceeding as described in Example 3, but replacing 2-fluorophenylacetic acid with 2-methoxyphenylacetic acid] in 2,4,6-collidine (250 ml) and the reaction mixture was heated to 165° C. After 3 h the reaction mixture was cooled to room temperature, and the product was extracted into ethyl acetate. The organic extract was washed with aqueous HCl (5%), $NaHCO_3$ and brine, and dried over $MgSO_4$. The organic solvent was removed in vacuo to give 2.25 g of crude product, which upon recrystallization from chloroform/hexanes gave pure 6-[3-(2,4,6-trichlorobenzoyl)-6-hydroxybenzyl]-2H-pyridazin-3-one (1.97 g) as a solid, mp 257.8° C.

Ethyl iodide (0.1 mL, 1.22 mmol) and potassium carbonate (0.253 g) were added to a solution of 6-[3-(2,4,6-trichlorobenzoyl)-6-hydroxybenzyl]-2H-pyridazin-3-one (0.50 g, 1.22 mmol) [prepared as described above] in acetone (50 ml) and the reaction mixture was heated to reflux. After 3 days the organics were evaporated and the residue was partitioned between ethyl acetate and water. The organic layer was separated and dried over $MgSO_4$. The solvent was removed in vacuo to give a mixture of 6-[3-(2,4,6-trichlorobenzoyl)-6-ethoxybenzyl]-2H-pyridazin-3-one and of 6-[3-(2,4,6-trichlorobenzoyl)-6-ethoxybenzyl]-2-ethyl-2H-pyridazin-3-one. 6-[3-(2,4,6-trichloro-benzoyl)-6-ethoxybenzyl]-2H-pyridazin-3-one was isolated by chromatography on a silica gel column (30% hexanes in ethyl acetate) as a solid (0.24 g), mp 163.5°–164.3° C.

EXAMPLE 7

Synthesis of 6-[3-(4-methylthio-benzoyl)-2-chlorobenzyl]-2H-pyridazin-3-one $NaSCH_3$ (0.047 g, 2 eq.) was added to a solution of 6-[3-(4-chlorobenzoyl)-2-chlorobenzyl]-2H-pyridazin-3-one (0.12 g, 0.33 mmol, 1 eq.) [prepared as described in Example 2] in dry DMF (1.5 ml) under a nitrogen atmosphere. The reaction mixture was stirred overnight at ambient temperature and then partitioned between EtOAc and 1M HCl. The organic layer was separated and washed with water and brine, and dried over $MgSO_4$. The solvent was removed in vacuo to give 6-[3-(4-methylthio-benzoyl)-2-chlorobenzyl]-2H-pyridizin-3-one (0.12 g) as an oil. Crystallized from acetone gave 6-[3-(4-methylthio-benzoyl)-2-chlorobenzyl]-2H-pyridazin-3-one (0.088 g, 72% yield) as tan crystals, mp 156.9° to 157.2° C.

EXAMPLE 8

Synthesis of 6-[3-(2,4,6-trichlorobenzoyl)benzyl]-2H-pyridazin-3-one 6-[3-(2,4,6-trichlorobenzoyl)-6-bromobenzyl]-2H-pyridazin-3-one (0.20 g) [prepared by proceeding as described in Example 3, but replacing 2-fluorophenylacetic acid with 2-bromophenylacetic acid] and 5% P/C (100 mg) were suspended in ethanol (20 ml). The mixture was stirred under a hydrogen atmosphere at ambient temperature and atmospheric pressure. After 3 h the catalyst was removed by filtration through celite and the filtrate was evaporated in vacuo. Chromatography on a silica gel column (30% acetone in methylene chloride) gave 6-[3-(2,4,6-trichlorobenzoyl)benzyl]-2H-pyridazin-3-one (0.12 g) as a solid, mp 149°–151° C.

EXAMPLE 9

The following are representative pharmaceutical formulations containing a compound of formula I.

Tablet formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Suspension formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s.to 100 ml |

Injectable formulation

The following ingredients are mixed to form an injectable formulation.

| Ingredient | Amount |
| --- | --- |
| compound of this invention | 0.2 g |
| sodium acetate buffer solution, 0.4M | 2.0 ml |
| HCl(1 N) or NaOH (1 N) | q.s. to suitable pH |
| water (distilled, sterile) | q.s. to 20 ml |

Topical formulation

A topical formulation is prepared with the following ingredients.

| Ingredient | Amount, g |
| --- | --- |
| compound of this invention | 10 |
| Span 60 | 2 |
| TWEEN ® 60 | 2 |
| mineral oil | 5 |
| petrolatum | 10 |
| methyl paraben | 0.15 |
| propyl paraben | 0.05 |
| BHA (butylated hydroxy anisole) | 0.01 |
| water | q.s. to 100 |

All of the above ingredients, except water, are combined and heated to 60°–70° C. with stirring. A sufficient quantity of water at 60° C. is then added with vigorous stirring to emulsify the ingredients, and water then added q.s. to 100 g.

Suppository formulation

A suppository of total weight 2.5 g is prepared by mixing the compound of the invention with Witepsol® (triglycerides of saturated vegetable fatty acid; Riches-Nelson, Inc., New York), and has the following composition:

| compound of the invention | 500 mg |
| --- | --- |
| Witepsol ® H-15 | balance |

EXAMPLE 10

Inhibition of COX I and COX II in vitro

The COX I and COX II inhibitory activity of compounds of this invention in vitro was determined using partially purified COX I and COX II enzymes, prepared as described in J. Barnett et al, Biochim. Biophys. Acta, 1209:130–139 (1994).

COX I and COX II samples were diluted with Tris-HCl buffer (50 mM Tris-HCl, pH 7.9) containing 2 mM EDTA and 10% glycerol and reconstituted by incubating first with 2 mM phenol for 5 minutes and then with 1 micromolar hematin for an additional 5 minutes. 125 $\mu$l of the reconstituted COX I or COX II enzyme were preincubated for 10 minutes at room temperature in a shaking water bath with the compounds of the invention dissolved in 2–15 $\mu$l of DMSO or the carrier vehicles (control samples). The enzyme reaction was initiated by adding 25 $\mu$l of 1-[14C] arachidonic acid (80,000–100,000 cpm/tube; 20 micromolar final concentration) and the reaction was allowed to continue for an additional 45 seconds. The reaction was terminated by adding 100 $\mu$l of 2N HCl and 750 $\mu$l water. An aliquot (950 $\mu$l) of the reaction mixture was loaded onto a 1 ml $C_{18}$ Sep-Pak column (J. T. Baker, Phillipsburg, N.J.) which had been previously washed with 2–3 ml methanol and equilibrated with 5–6 ml distilled water. Oxygenated products were quantitatively eluted with 3 ml of acetonitrile/water/acetic acid (50:50:0.1, v/v) and the radioactivity in the eluate determined in a scintillation counter.

Compounds of this invention were active in this assay.

The COX inhibitory activities (expressed as $IC_{50}$, the concentration causing 50% inhibition of the COX enzyme being assayed) of some compounds of the invention and indomethacin as a comparator, were:

| | $IC_{50}, \mu M$ | |
| --- | --- | --- |
| Cpd # | COX I | COX II |
| 2 | 57 | 0.1 |
| 11 | 391 | 1.8 |
| 26 | 540 | 0.6 |
| 28 | 100 | 2.0 |
| 31 | 1000 | 1.3 |
| 39 | 100 | 1.0 |
| 44 | 100 | 1.3 |
| 61 | 310 | 0.18 |
| 62 | 300 | 0.18 |
| 73 | 423 | 0.16 |
| 77 | 300 | 0.14 |
| 78 | 740 | 2.0 |
| Indomethacin | 0.4 | 14 |

EXAMPLE 11

Inhibition of COX I and COX II in a Cell Based Assay:

The COX I and COX II inhibitory activity of compounds of this invention in a cell based assay was determined as described below.

COX-I:

The inhibitory activity of the test compounds against cell associated COX-1 was measured using human promonocytic THP cells. Cells were plated in 96-well microtiter plates at a density of $8 \times 10^4$ cells/well in RPMI-1640 medium (Gibco). COX-1 activity was initiated by incubating the cells with 0.1$\mu$M phorbol 12-myristate 13-acetate (PMA, Sigma) in dimethyl sulfoxide (DMSO, Aldrich) at 37° C. After 40–48 hours, the medium was removed, and the cells were washed twice with phosphate buffered saline (PBS, Gibco). 225 $\mu$l/well of fresh medium containing desired concentrations of the test compounds in DMSO, or the carrier vehicles (control wells), was added and the cells incubated at 37° C. for 30 minutes; after which 5 $\mu$M calcium ionophore A23187 (Sigma) was added and the incubation was continued for an additional 10 minutes. The reaction was terminated by transferring the plates to ice. The culture supernatants were transferred and appropriately diluted and the amount of thromboxane $B_2$ ($TXB_2$) present in each supernatant was quantitated using an ELISA kit (Cayman Chemicals).

COX-II:

The inhibitory activity of test compounds against cell associated COX-2 was measured using primary cultures of human foreskin fibroblasts (HFF). HFF cultures were obtained from ATCC, grown in DMEM medium (Gibco) and used between 13–30 passages. Cells were plated in 96-well microtiter plates at a density of $6-8\times10^4$ cells/well in DMEM containing 10% fetal calf serum (Sigma) and cultured at 37° C. until they became confluent. The medium was removed and the cells were washed once with PBS. COX-2 activity was induced by incubating the cells with fresh DMEM containing 0.1 $\mu$M phorbol 12-myristate 13-acetate (PMA, Sigma) and 1ng/ml of human interleukin-1 (Sigma) at 37° C. After 16 h the medium was removed and the cells were washed twice with phosphate buffered saline (PBS, Gibco). 200 $\mu$l/well of fresh medium containing desired concentrations of the test compounds in DMSO, or the carrier vehicle (control wells) was added and the cells incubated at 37° C. for 30 minutes; after which 5 $\mu$M calcium ionophore A23187 (Sigma) was added and the incubation was continued for an additional 10 minutes. The reaction was terminated by transferring the plates to ice. The culture supernatants were transferred and appropriately diluted, and the amount of prostaglandin $E_2$ ($PGE_2$) present in each supernatant was quantitated using an ELISA kit (Cayman Chemicals).

Compounds of this invention were active in this assay.

The COX I and COX II inhibitory activities in the cell based assay (expressed as $IC_{50}$) of some compounds of the invention were:

| | $IC_{50}$, $\mu$M | |
| --- | --- | --- |
| Cpd # | COX I | COX II |
| 11 | 4.8 | 2 |
| 26 | 19 | 0.3 |
| 28 | NA | 3.4 |
| 31 | NA | 4 |
| 39 | 26 | 1.0 |
| 44 | 16 | 1.2 |
| 61 | NA | 0.48 |
| 62 | NA | 0.3 |
| 73 | 21 | 0.2 |
| 77 | 17 | 0.03 |
| 78 | NA | 0.3 |

NA = not available

EXAMPLE 12

Anti-inflammatory activity

The anti-inflammatory activity of compounds of this invention was determined by measuring the inhibition of carrageenan-induced paw edema in the rat, using a modification of the method described in Winter C. k et al (1962) "Carrageenan-Induced Edema in Hind Paw of the Rat as an Assay for Anti-inflammatory Drugs". *Proc. Soc. Exp. Biol. Med.* 111: 544–547. This assay has been used as a primary in vivo screen for anti-inflammatory activity of most NSAIDs, and is considered predictive of human efficacy. Briefly, test materials were administered orally to female rats in a volume of 1 ml prepared as solutions or suspensions in an aqueous vehicle containing 0.9% NaCl, 0.5% sodium carboxymethyl-cellulose, 0.4% polysorbate 80, 0.9% benzyl alcohol and 97.3% distilled water. Control rats received vehicle alone. After 1 hr 0.05 ml of a 0.5% solution of Carrageenan (Type IV Lambda, Sigma Chemical Co.) in 0.9% saline was injected into the subplantar region of the right hind paw. Three hours later the rats were euthanized in a carbon dioxide atmosphere; hind paws were removed by severing at the tatso-crural joint; and the left and right paws were weighed. The increase in weight of the right paw over the left paw was obtained for each animal and the mean increases were calculated for each group. The anti-inflammatory activity of the test materials is expressed as the percent inhibition of the increase in hind paw weight of the test group relative to the vehicle-dosed control group. Compounds of this invention were active in this assay.

The anti-inflammatory activities (expressed as % inhibition) of some of the compounds of the invention were:

| Cpd # | Dose mg/Kg | % inhibition |
| --- | --- | --- |
| 2 | 10 | 20 |
| 11 | 10 | 44 |
| 26 | 30 | 24 |
| 28 | 30 | 21 |
| 31 | 30 | 38 |
| 39 | 30 | 33 |
| 44 | 30 | 19 |
| 62 | 30 | 33 |
| 73 | 30 | 33 |
| 78 | 30 | 22 |

EXAMPLE 13

Inhibition of eicosanoid synthesis in vivo

The activity of compounds of this invention in inhibiting in vivo eicosanoid (prostaglandin $E_2$) synthesis in inflamed tissues was determined by the carrageenan-induced inflammation (air-pouch model) in rats, using a modification of the method described in Futaii, M., et al; (1993) "Selective Inhibition of NS-398 on prostanoid production in inflamed tissue in rat Carrageenan Air-pouch Inflammation" *J. Pharm. Pharmacol.* 45:753–755, and Masferrer, J. L., et aL; (1994) "Selective Inhibition of inducible cyclooxygenase 2 in vivo is Antiinflammatory and Nonulcerogenic" *Proc. Natl. Acad. Sci. USA.* 91: 3228–3232. In this assay, an air-pouch is created in the rat and the $PGE_2$ levels in the air-pouch exudate are measured by enzyme immunoassay. Briefly, male rats were anesthetized using a 60:40 $CO_2$:$O_2$ mixture and subsequently injected subcutaneously with 20 ml of sterilized air, under aseptic conditions, in the proximal area of the dorsum. This injection of sterile air causes the creation of a subcutaneous "air pouch". The next day, a further 10 ml of sterile air was injected into the previously formed pouch using the same technique. The test materials were administered orally in a volume of 1 ml/100 g body weight as solutions or suspensions in an aqueous vehicle containing 0.9% NaCl, 0.5% sodium carboxymethyl-cellulose, 0.4% polysorbate 80,0.9% benzyl alcohol and 97.3% water. Control rats received vehicle alone. After 30 minutes, 5 ml of a 0.5% solution of carrageenan (Sigma, Lambda Type IV) was injected into the air pouch. The rats were euthanized 3 hr after the compound administration. 10 ml of a solution containing 10 $\mu$g/l of indomethacin and 5.4 mM EDTA in 0.9% sterile saline was injected into the air pouch; the air pouch was cut open; and the exudate was harvested. The total exudate volume was recorded, and the samples were analyzed for $PGE_2$ and 6-keto $PGF_1$ by ELISA (Titerzyme®, PerSeptive Diagnostics) and $TxB_2$ by radio-immuno assay ( New England Nuclear Research, Catalog No. NEK-037), according to the manufacturer's directions.

The mean concentrations of $PGE_2$ were calculated for each group. The anti-inflammatory activity of test materials is expressed as the percent inhibition of $PGE_2$ formation in the test group relative to the control group.

Compounds of this invention were active in this assay.

The anti-inflammatory activities (expressed as % inhibition of air pouch $PGE_2$ formation) of some of the compounds of this invention and indomethacin as a comparator were:

| Cpd # | Dose mg/Kg | % ihibition |
|---|---|---|
| 2 | 10 | 32% |
| 5 | 10 | 32% |
| 10 | 10 | 24% |
| 11 | 10 | 80% |
| 77 | 30 | 53% |
| Indomethacin | 2–5 | >70% |

EXAMPLE 14

Analgesic Activity

The analgesic activity of compounds of this invention may be determined by the Acetic Acid-induced Rat Writhing Assay, using a modification of the method described in Berkenkopf, J. W. and Weichman, B. M. "Production of Prostacyclin in Mice following Intraperitoneal Injection of Acetic Acid, Phenylbenzoquinone and Zymosan: Its Role in the Writhing Response". *Prostaglandins:* 36: 693–70 (1988). This assay is one of several acute assays which have been used to assess the analgesic activity of NSAIDs, and is considered predictive of human efficacy. The test materials were administered orally to male Sprague Dawley rats in a volume of 1 ml/100 g body weight as solutions or suspensions in an aqueous vehicle containing 0.9% NaCl, 0.5% sodium carboxymethyl-cellulose, 0.4% polysorbate 80, 0.9% benzyl alcohol and 97.3% water. Control rats received vehicle alone. One hour after compound administration, 0.3 ml/100 g body weight of 0.75% solution of acetic acid was injected intraperitoneally. The acetic acid injection induces a series of characteristic writhing responses, which were counted over the period between 15 and 30 minutes after the injection. The analgesic activity of test materials is expressed as the percentage inhibition of writhing in the test group relative to the control group.

Compounds of this invention were active in this assay.

The analgesic activities (expressed as % inhibition of writhing responses) of some of the compounds of this invention at 10 mg/Kg were:

| Cpd # | % inhibition |
|---|---|
| 2 | 9 |
| 11 | 10 |

The analgesic activity of compounds of this invention may also be determined using an adjuvant-induced arthritis pain model in the rat, where pain is assessed by the animal's vocal response to the squeezing or flexing of an inflamed ankle joint, as described in Winter C. A., and Nuss, G. W. (1966) "Treatment of Adjuvant Arthritis in rats with Anti-inflammatory Drugs". *Arthritis Rheum.* 9: 394–403, and Winter, C. A, Kling P. J., Tocco, D. J., and Tanabe, K (1979). "Analgesic activity of Diflunisal [MK-647; 5-(2,4-Difluorophenyl)salicylic acid] in Rats with Hyperalgesia Induced by Freund's Adjuvant". *J. Pharnacol. Exp. Ther.* 211: 678–685.

What is claimed is:

1. A compound selected from the group of compounds represented by formula I:

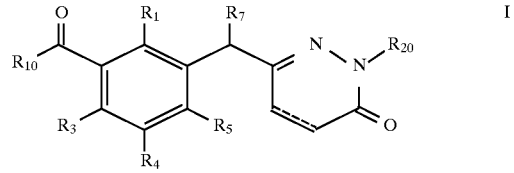

where:

the dashed line denotes an optional bond;

$R_1$ is H, halo, alkyl, alkyloxy, amino, alkylamino, dialkylamino, or acylamino;

$R_3$ and $R_4$ are independently H, halo, alkyl, alkyloxy, or hydroxy;

$R_5$ is H, halo, alkyl, alkylthio, alkyloxy, alkenyloxy, alkynyl, or alkenyl; provided that at least one of $R_1$, $R_3$, $R_4$, and $R_5$ is H;

$R_7$ is H, alkyl, cyano, or amido;

$R_{10}$ is a group represented by formula (A), (B), or (C):

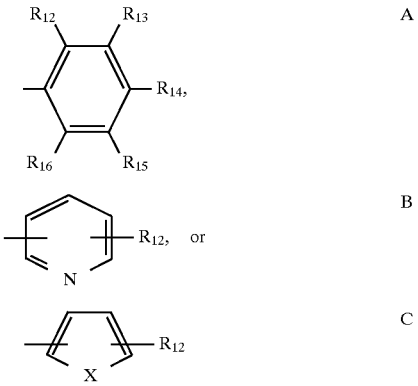

where:

X is O or S;

$R_{12}$, $R_{13}$, $R_{15}$, and $R_{16}$ are independently H, halo, alkyl, alkyloxy, or alkylthio; and $R_{14}$ is H, halo, alkyl, alkylthio, alkyloxy, alkenyloxy, alkynyl, alkenyl, or —$SO_2R_{17}$ where $R_{17}$ is alkyl, or —$SO_2NR_{18}R_{19}$ where $R_{18}$ and $R_{19}$ are independently H or alkyl; provided that at least two of $R_{12}$, $R_{13}$, $R_{14}$, $R_{15}$, and $R_{16}$ are H, and that if only two of $R_{12}$, $R_{13}$, $R_{14}$, $R_{15}$, and $R_{16}$ are H, the non-hydrogen substituents are not all adjacent; and at least one of $R_{12}$ and $R_{16}$ is H when neither $R_1$ nor $R_3$ are H; and $R_{20}$ is H, alkyl, haloalkyl, hydroxyalkyl, or alkenyl; and their pharmaceutically acceptable salts.

2. The compound of claim 1 wherein, $R_{10}$ is a group represented by formula (A) and the optional bond is present.

3. The compound of claim 2 wherein, $R_4$, $R_{13}$ and $R_{15}$ are H.

4. The compound of claim 3 wherein, $R_7$ is H, alkyl, or cyano; and $R_{20}$ is H or alkyl.

5. The compound of claim 4 wherein, $R_7$ is H, Me, or cyano; and $R_{20}$ are H or Me.

6. The compound of claim 5 wherein, $R_1$ and $R_3$ are independently H, halo, or alkyl.

7. The compound of claim 6 wherein, $R_5$, $R_{12}$, $R_{14}$, and $R_{16}$ are independently H, halo, alkyl, alkyloxy, or alkylthio.

8. The compound of claim 7 wherein, $R_1$ and $R_3$ are independently H, Cl, or Me; and $R_{12}$ and $R_{16}$ are independently H, Cl, Br, Me, OMe, or SMe.

9. The compound of claim 8 wherein, $R_5$ and $R_{14}$ are independently H, F, Cl, Me, OMe, or SMe.

10. The compound of claim 9 wherein, $R_{12}$, $R_{16}$, and $R_{20}$ are H; and $R_7$ is H or cyano.

11. The compound of claim 9 wherein, $R_1$ and $R_3$ are H; and $R_7$ and $R_{20}$ are independently H or Me.

12. The compound of claim 10 wherein, $R_3$ and $R_5$ are H.

13. The compound of claim 12 wherein, $R_1$ is Cl or Me; and $R_{14}$ is Cl, OMe, or SMe.

14. The compound of claim 13 wherein, $R_7$ is H.

15. The compound of claim 14 wherein, $R_{14}$ is OMe.

16. The compound of claim 15 wherein $R_1$ is Cl namely, 6-{3-(4-methoxybenzoyl)-2-chlorobenzyl}-2H-pyridazin-3-one.

17. The compound of claim 15 wherein, $R_1$ is Me namely, is 6-{3-(4-methoxybenzoyl)-2-methylbenzyl}-2H-pyridazin-3-one.

18. The compound of claim 11 wherein, $R_5$ is H, F, Cl, Me, or OMe; and $R_{12}$ and $R_{16}$ are independently Cl, Br, or Me; and $R_{14}$ is Cl, Me, or OMe.

19. The compound of claim 18 wherein, $R_7$ is H.

20. The compound of claim 19 wherein, $R_{12}$, $R_{14}$, and $R_{16}$ are independently Cl or Me; and $R_{20}$ is H.

21. The compound of claim 20 wherein, $R_{12}$, $R_{14}$ and $R_{16}$ are Cl and $R_5$ is F namely, 6-{3- (2,4,6-trichlorobenzoyl)-6-fluorobenzyl)}-2H-pyridazin-3-one.

22. The compound of claim 20 wherein, $R_{12}$, $R_{14}$, and $R_{16}$ are Cl and $R_5$ is OMe namely, 6-{3-(2,4,6-trichlorobenzoyl)-6-methoxybenzyl}-2H-pyridazin-3-one.

23. A pharmaceutical composition comprising a therapeutically effective amount of a compound of claim 1 and a pharmaceutically acceptable excipient.

24. A method of treatment of a disease in a mammal treatable by administration of a prostaglandin G/H synthase inhibitor, comprising administration to the mammal of a therapeutically effective amount of a compound of claim 1.

25. The method of claim 24 wherein, the disease is an inflammatory disease or an autoimmune disease.

26. A method of treatment of a disease in a mammal treatable by administration of a prostaglandin G/H synthase inhibitor, comprising administration to the mammal of a therapeutically effective amount of a compound of claim 17.

* * * * *